(12) United States Patent
Rioux et al.

(10) Patent No.: US 9,375,217 B2
(45) Date of Patent: Jun. 28, 2016

(54) CATHETERIZING BODY LUMENS

(75) Inventors: Robert F. Rioux, Ashland, MA (US); David J. Sauvageau, Methuen, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1398 days.

(21) Appl. No.: 11/458,171

(22) Filed: Jul. 18, 2006

(65) Prior Publication Data
US 2008/0051758 A1 Feb. 28, 2008

(51) Int. Cl.
*A61B 17/12* (2006.01)
*A61B 17/34* (2006.01)
(Continued)

(52) U.S. Cl.
CPC ..... *A61B 17/12109* (2013.01); *A61B 17/12022* (2013.01); *A61B 17/12031* (2013.01); *A61B 17/12045* (2013.01); *A61B 17/12136* (2013.01); *A61B 17/12186* (2013.01); *A61B 17/1214* (2013.01); *A61B 17/3468* (2013.01); *A61B 2017/00557* (2013.01); *A61B 2017/12127* (2013.01); *A61B 2017/22052* (2013.01); *A61B 2017/22065* (2013.01); *A61M 25/0606* (2013.01); *A61M 2025/1052* (2013.01); *A61M 2210/1071* (2013.01); *A61M 2210/12* (2013.01)

(58) Field of Classification Search
CPC ............ A61B 17/12031; A61B 17/12045; A61B 17/12109; A61B 2017/12127; A61B 17/12136; A61B 17/1214; A61B 17/12186; A61M 2025/1052; A61M 2210/1071; A61M 2210/12
USPC .............. 604/500, 523, 525, 509, 508, 96.01, 604/264, 510, 506, 507, 103.06, 164.01, 604/164.13, 170.03, 528, 93.01, 97.01, 604/164.03, 19, 48, 907, 912, 915
See application file for complete search history.

(56) References Cited

U.S. PATENT DOCUMENTS 4,501,263 A * 2/1985 Harbuck .................. 128/898
4,897,255 A 1/1990 Fritzberg et al.
(Continued)

FOREIGN PATENT DOCUMENTS

EP 1 498 455 1/2005
JP 2003250896 A * 9/2003
(Continued)

OTHER PUBLICATIONS

"Intra-arterial Therapy" *American Cancer Society Cancer Medicine*; http://www.ncbi.nlm.nih.gov/books/bv.fcgi?rid=cmed.section.7252 (Jan. 18, 2006).
(Continued)

*Primary Examiner* — Kevin C Sirmons
*Assistant Examiner* — Shefali Patel
(74) *Attorney, Agent, or Firm* — Seager, Tufte & Wickhem, LLP

(57) ABSTRACT

A method and related medical devices include delivering a catheter into a lumen of a subject. The catheter can include a generally tubular member having a lumen, a proximal region, and a distal region, and an inflatable member carried by a portion of the generally tubular member. The method can also include curving the portion of the generally tubular member that carries the inflatable member within the lumen of the subject, and disposing a material (e.g., an embolic material or a contrast agent) into the lumen of the generally tubular member.

26 Claims, 10 Drawing Sheets

(51) Int. Cl.
*A61B 17/00* (2006.01)
*A61B 17/22* (2006.01)
*A61M 25/06* (2006.01)
*A61M 25/10* (2013.01)

(56) References Cited

U.S. PATENT DOCUMENTS

| | | | |
|---|---|---|---|
| 4,983,166 A * | 1/1991 | Yamawaki | 604/99.04 |
| 5,207,647 A * | 5/1993 | Phelps | 604/158 |
| 5,254,091 A * | 10/1993 | Aliahmad et al. | 604/103.06 |
| 5,306,246 A | 4/1994 | Sahatjian et al. | |
| 5,425,708 A * | 6/1995 | Nasu | 604/102.03 |
| 5,630,802 A * | 5/1997 | Moellmann et al. | 604/164.01 |
| 5,702,361 A * | 12/1997 | Evans et al. | 604/508 |
| 5,733,925 A | 3/1998 | Kunz et al. | |
| 5,814,016 A * | 9/1998 | Valley et al. | 604/96.01 |
| 5,891,027 A * | 4/1999 | Tu et al. | 600/374 |
| 6,010,479 A * | 1/2000 | Dimitri | A61J 15/0015 604/525 |
| 6,048,331 A * | 4/2000 | Tsugita et al. | 604/102.03 |
| 6,072,004 A | 6/2000 | Migchels et al. | |
| 6,086,548 A * | 7/2000 | Chaisson et al. | 600/585 |
| 6,093,173 A * | 7/2000 | Balceta et al. | 604/164.01 |
| 6,129,713 A * | 10/2000 | Mangosong et al. | 604/264 |
| 6,368,658 B1 | 4/2002 | Schwarz et al. | |
| 6,656,550 B1 * | 12/2003 | Zamore | 428/35.7 |
| 6,722,370 B1 * | 4/2004 | Mann | 128/898 |
| 6,746,464 B1 | 6/2004 | Makower | |
| 6,827,711 B2 * | 12/2004 | Sunseri | 604/509 |
| 6,951,675 B2 | 10/2005 | Chin et al. | |
| 6,966,902 B2 * | 11/2005 | Tsugita et al. | 604/509 |
| 7,488,339 B2 | 2/2009 | St. Pierre et al. | |
| 2001/0023334 A1 | 9/2001 | St. Goar et al. | 604/101.04 |
| 2002/0072763 A1 | 6/2002 | Chien et al. | 606/194 |
| 2002/0165523 A1 | 11/2002 | Chin et al. | |
| 2004/0076582 A1 | 4/2004 | DiMatteo et al. | |
| 2004/0078052 A1 | 4/2004 | St. Pierre et al. | |
| 2004/0091543 A1 * | 5/2004 | Bell et al. | 424/489 |
| 2004/0096662 A1 | 5/2004 | Lanphere et al. | |
| 2004/0101564 A1 | 5/2004 | Rioux et al. | |
| 2004/0116851 A1 * | 6/2004 | Johansen et al. | 604/103.04 |
| 2004/0138614 A1 * | 7/2004 | Hahnen | 604/96.01 |
| 2004/0146670 A1 | 7/2004 | Chin et al. | |
| 2004/0181189 A1 | 9/2004 | Roychowdhury et al. | |
| 2004/0186377 A1 | 9/2004 | Zhong et al. | |
| 2004/0267196 A1 | 12/2004 | Miki et al. | |
| 2005/0095428 A1 | 5/2005 | Dicarlo et al. | |
| 2005/0131446 A1 | 6/2005 | Coughlin et al. | |
| 2005/0131450 A1 | 6/2005 | Nicholson et al. | |
| 2005/0158272 A1 | 7/2005 | Whirley et al. | |
| 2005/0196449 A1 * | 9/2005 | Dicarlo et al. | 424/486 |
| 2005/0197667 A1 | 9/2005 | Chan et al. | |
| 2005/0197668 A1 | 9/2005 | Lim et al. | |
| 2006/0045900 A1 | 3/2006 | Richard et al. | |
| 2006/0171985 A1 | 8/2006 | Richard et al. | |
| 2006/0199010 A1 | 9/2006 | DiCarlo et al. | |
| 2007/0005010 A1 * | 1/2007 | Mori et al. | 604/102.01 |
| 2007/0111605 A1 | 5/2007 | Zhang et al. | |
| 2007/0141099 A1 | 6/2007 | Buiser et al. | |
| 2007/0141339 A1 | 6/2007 | Song et al. | |
| 2007/0141340 A1 | 6/2007 | Song | |
| 2007/0142560 A1 | 6/2007 | Song et al. | |

FOREIGN PATENT DOCUMENTS

| | | |
|---|---|---|
| WO | 02/47731 | 6/2002 |
| WO | 2005/057272 | 6/2005 |

OTHER PUBLICATIONS

Dixon, "Liver Cancer Treatment" http://ww.livercancertreatment. org/treatment/embolization.asp (2003).

Madoff et al., "Portal Vein Embolization with Polyvinyl Alcohol Particles and Coils in Preparation for Major Liver Resection for Hepatobiliary Malignancy: Safety and Effectiveness—Study in 26 Patients" *Radiology* 251-260 (2003).

Madoff et al., "Transhepatic Ipsilateral Right Portal Vein Embolization Extended to Segment IV: Improving Hypertrophy and Resection Outcomes with Spherical Particles and Coils" *J. Vasc. Interv. Radiol.* 16:215-225 (2005).

Madoff, "Preoperative Portal Vein Embolization" *Endovascular Today* 70-80 (2005).

Ming-De et al. "Study of portal vein embolization with absolute ethanol injection in cirrhotic rats" *WJG* 4(5):415-417 (1998).

Satake et al., "Percutaneous Transhepatic Portal Vein Embolization: Effectiveness of Absolute Ethanol Infusion with Balloon Catheter in a Pig Model" *Acta Radiologica* 46(4):344-352(9) (2005).

Shukla, "Conservation in hepatic cancer" *Indian J. Surg.* 65:344-346 (2003).

* cited by examiner

CATHETERIZING BODY LUMENS

TECHNICAL FIELD

This invention relates to medical devices, and to related components and methods.

BACKGROUND

Therapeutic vascular occlusions (embolizations) are used to prevent or treat pathological conditions in situ. Compositions including embolic particles are used for occluding vessels in a variety of medical applications. Embolic particles can be delivered to a target site in a body of a subject using, for example, a catheter.

SUMMARY

In one aspect, the invention features a method that includes delivering a catheter into a lumen of a subject. The catheter includes a generally tubular member having a lumen, a proximal region, and a distal region, and an inflatable member carried by a portion of the generally tubular member. The method also includes curving the portion of the generally tubular member that carries the inflatable member within the lumen of the subject, and disposing at least one embolic material into the lumen of the generally tubular member.

In another aspect, the invention features a method that includes delivering a catheter into a lumen of a subject. The catheter includes a generally tubular member having a lumen, a proximal region, and a distal region, and an inflatable member carried by a portion of the generally tubular member. The method also includes curving the portion of the generally tubular member that carries the inflatable member within the lumen of the subject, and flowing at least one contrast agent into the lumen of the generally tubular member.

In an additional aspect, the invention features a method of resecting liver tissue of a subject. The method includes delivering a catheter into a lumen of a subject. The catheter includes a generally tubular member having a lumen, a proximal region, and a distal region, and an inflatable member that is carried by a portion of the generally tubular member. The method also includes inflating the inflatable member within the lumen of the subject, curving the portion of the generally tubular member that carries the inflatable member within the lumen of the subject, disposing embolic particles into the lumen of the generally tubular member, delivering the embolic particles into the lumen of the subject, and resecting liver tissue of the subject.

Embodiments can also include one or more of the following.

The embolic material can include one or more embolic gels, embolic particles, and/or embolic coils. The embolic particles can have an arithmetic mean diameter of about 3,000 microns or less and/or about one micron or more.

The method can include disposing at least one embolic material into the lumen of the generally tubular member, and/or delivering at least one embolic material into the lumen of the subject. The method can include rotating the portion of the generally tubular member that carries the inflatable member within the lumen of the subject. During and/or after rotation of the portion of the generally tubular member, at least one embolic material can be disposed into the lumen of the generally tubular member, and/or at least one contrast agent can be flowed through the lumen of the generally tubular member. The method can include viewing the embolic material (e.g., within the lumen of the subject) using X-ray fluoroscopy. The method can include resecting liver tissue of the subject.

Curving the portion of the generally tubular member that carries the inflatable member can include removing an inner member from the lumen of the generally tubular member, and/or disposing an inner member into the lumen of the generally tubular member. The inner member can include a needle, a guidewire, a stylet, or a combination thereof. Curving the portion of the generally tubular member that carries the inflatable member can include inflating the inflatable member and/or aligning the portion of the generally tubular member with a longitudinal axis of the lumen of the subject.

The method can include inflating the inflatable member. The method can include delivering at least one embolic material and/or contrast agent into the lumen of the generally tubular member during and/or after inflation of the inflatable member. When inflated, the inflatable member can have a diameter of at least about one centimeter (e.g., at least about two centimeters, at least about three centimeters) and/or at most about four centimeters (e.g., at most about three centimeters, at most about two centimeters). The inflatable member can have a wall including at least two regions with different thicknesses. The inflatable member can be eccentrically disposed on the portion of the generally tubular member that carries the inflatable member.

The distal region of the generally tubular member can include a distal end of the generally tubular member, and the lumen of the generally tubular member can extend through the distal end of the generally tubular member.

The lumen of the subject can be a branch of a portal vein. The lumen of the subject can have a longitudinal axis. Delivering the catheter into the lumen of the subject can include inserting the catheter into the lumen of the subject along an axis that is perpendicular to the longitudinal axis of the lumen of the subject. Delivering the catheter into the lumen of the subject can include inserting the catheter through a location in the skin of the subject and through a location in the lumen of the subject. The location in the lumen of the subject can be located at most about three millimeters (e.g., at most about two millimeters, at most about one millimeter), and/or at least about 0.1 millimeter (e.g., at least about 0.5 millimeter, at least about one millimeter), from the location in the skin of the subject.

Embodiments can include one or more of the following advantages.

The method can be used to deliver one or more embolic materials, contrast agents, and/or therapeutic agents to a target site (e.g., a lumen of a subject) effectively and efficiently. Curving the distal region of the generally tubular member can allow the embolic materials, contrast agents, and/or therapeutic agents to be delivered into the target site relatively easily and/or in a relatively high volume.

The method can include embolizing one or more branches of a portal vein. The embolization of the branches of the portal vein can be executed relatively efficiently and with a relatively low likelihood of harm to the subject (e.g., with a relatively low likelihood of perforation of the walls of the branches). In some embodiments, one or more branches of a portal vein of a subject can be embolized prior to a liver resection procedure. This can, for example, enable one or more segments of the liver of the subject to be resected with relatively little blood loss, and/or enable one or more non-resected segments of the liver of the subject to experience a relatively high rate of growth.

The distance between the point at which the catheter enters the body of a subject and the point at which the catheter enters a target site (e.g., a lumen of the subject, such as a branch of a portal vein) can be relatively short. As a result, the catheter can be delivered into a target site without having to navigate a long distance within the body of the subject first. This can, for example, reduce procedure time and/or result in a relatively low likelihood of injury to the subject.

The method can be used to provide a targeted area for embolization, therapeutic agent delivery, and/or contrast agent delivery. For example, in some embodiments, a catheter can be used to occlude a portion of a lumen of a subject and to deliver one or more embolic materials, therapeutic agents, and/or contrast agents into a specific region of the lumen of the subject that is defined by the occlusion.

The method can include occluding a lumen of a subject, such as a branch of a portal vein, without using X-ray fluoroscopy prior to or during the occlusion. In some embodiments, the method can include using ultrasound to locate a lumen of a subject, such as a branch of a portal vein, and percutaneously inserting a balloon catheter into the lumen after identifying its location.

The method can include inflating an eccentrically disposed balloon of a balloon catheter within a lumen of a subject, and the eccentricity of the balloon can cause the inflated balloon to be relatively unlikely to slip and/or become dislodged from its location within the lumen of the subject.

Features and advantages are in the description, drawings, and claims.

DETAILED DESCRIPTION

Figure 1:
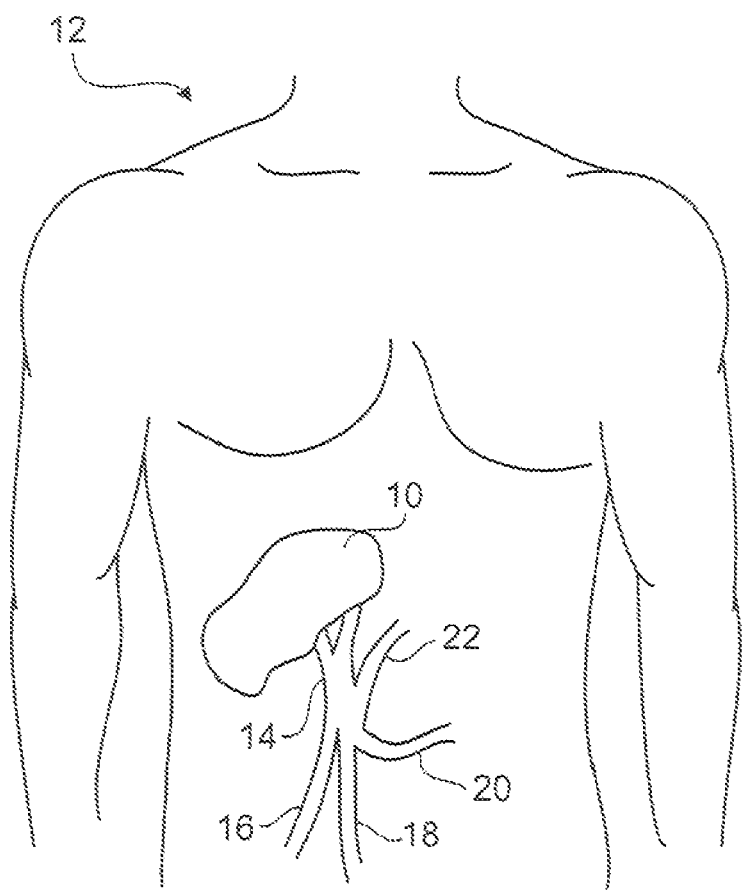
FIG. 1 is an illustration of a liver of a subject.

FIG. 1 shows a liver 10 of a subject 12, as well as a portal vein 14, a superior mesenteric vein 16, an inferior mesenteric vein 18, a splenic vein 20, and a gastric vein 22. Portal vein 14, which is formed by the union of superior mesenteric vein 16 and splenic vein 20, drains blood into liver 10. Portal vein 14 has many different branches that extend into, and provide blood to, different segments of liver 10.

In some embodiments, it may be desirable to embolize one or more of the branches of portal vein 14. For example, in certain embodiments, prior to a procedure in which one or more segments of liver 10 are to be resected (e.g., because they are tumorous), one or more of the branches of portal vein 14 can be embolized. This embolization of selected branches of portal vein 14 can be used to slow or stop blood flow to segments of liver 10 that will be resected, and to redirect blood flow to segments of liver 10 that will not be resected. The redireaction of blood flow to segments of liver 10 that will not be resected can initiate hypertrophy, or exaggerated growth, of those segments. The hypertrophy can be used to develop healthy liver tissue prior to resection of unhealthy liver tissue.

FIGS. 2A-2D illustrate a procedure that can be used to embolize a branch 24 of portal vein 14.

Figure 2A:
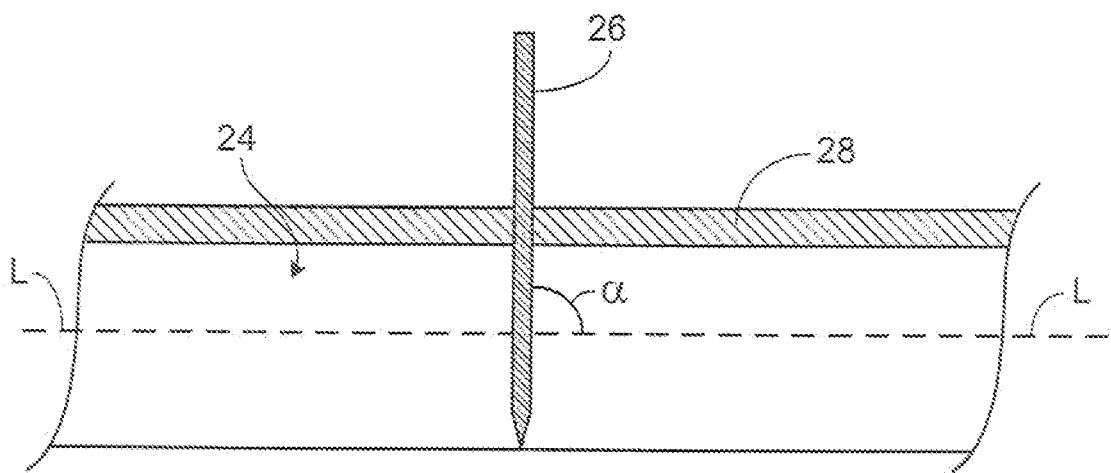
FIG. 2A illustrates the delivery of an embodiment of a needle into a lumen of a subject.

First, branch 24 is located using ultrasound. Then, as shown in FIG. 2A, a needle 26 (e.g., a diagnostic needle from an AccuStick™ Introducer System from Boston Scientific Corp.) is inserted through a layer 28 formed of skin and/or tissue, and into branch 24. Branch 24 has a longitudinal axis L, and needle 26 is inserted into branch 24 at an angle α that is perpendicular to longitudinal axis L.

Figure 2B:
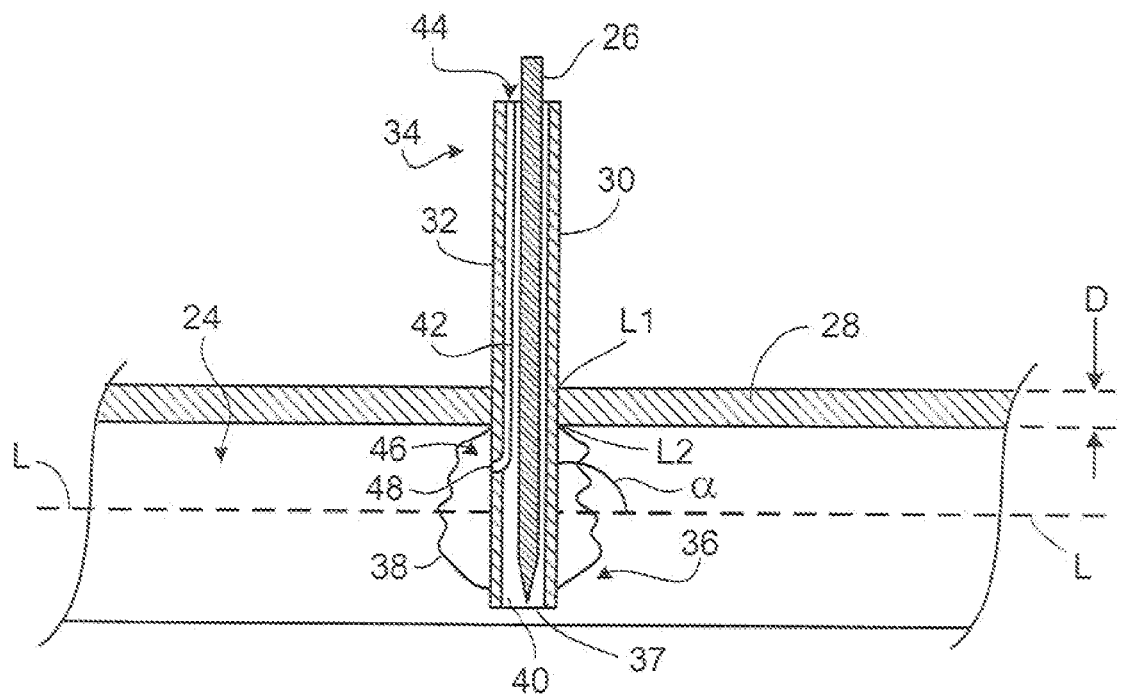
FIG. 2B illustrates the delivery of an embodiment of balloon catheter into the lumen of the subject of FIG. 2A.

As shown in FIG. 2B, a balloon catheter 30 is then inserted over needle 26 and into branch 24, also at an angle α that is perpendicular to longitudinal axis L of branch 24. Balloon catheter 30 enters layer 28 at a location L1 and enters branch 24 at a location L2. Typically, the distance D between location L1 and location L2 can be relatively short, such that balloon catheter 30 does not have to navigate a long and/or tortuous path to reach branch 24. In some embodiments, distance D can be at most about three millimeters (e.g., at most about two millimeters) and/or at least about one millimeter (e.g., at least about two millimeters). The delivery of balloon catheter 30 into branch 24, and/or the location of balloon catheter 30 within branch 24, can be confirmed using, for example, ultrasound.

As shown in FIG. 2B, balloon catheter 30 includes a generally tubular member 32 having a proximal region 34 and a distal region 36 including the distal end 37 of generally tubular member 32. Balloon catheter 30 also includes a balloon 38 that is disposed on distal region 36 of generally tubular member 32. Generally tubular member 32 has a central lumen 40 that allows generally tubular member 32 to be inserted over needle 26. Generally tubular member 32 also has an inflation lumen 42 including a proximal end 44 and a distal end 46. Distal end 46 forms an opening 48 in generally tubular member 32, such that inflation lumen 42 is in fluid communication with balloon 38.

Figure 2C:
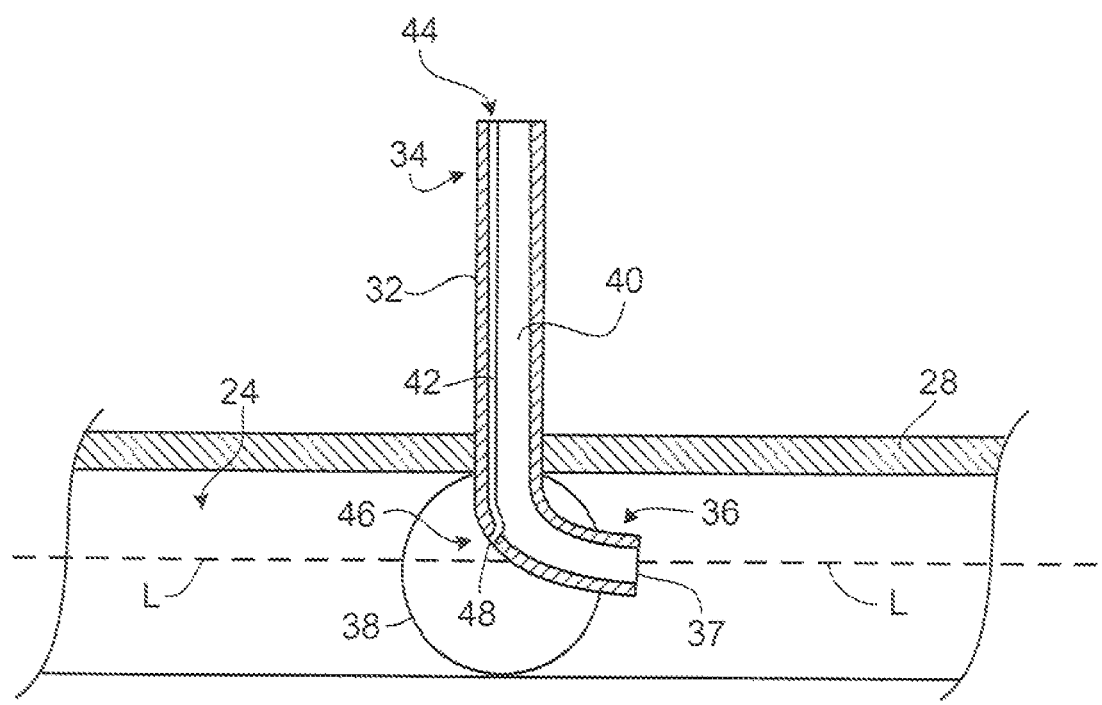
FIG. 2C illustrates the inflation of a balloon of the balloon catheter of FIG. 2B within the lumen of the subject.

After balloon catheter 30 has been inserted into branch 24 of portal vein 14, needle 26 is removed from central lumen 40 of generally tubular member 32. As shown in FIG. 2C, balloon 38 is inflated by flowing inflation fluid (e.g., a saline solution mixed with a radiopaque contrast agent) through inflation lumen 42. The removal of needle 26 from generally tubular member 32, and the inflation of balloon 28, cause distal region 36 of generally tubular member 32 to become curved so that it is aligned with longitudinal axis L of branch 24. Appropriate alignment can be achieved by positioning a guidewire, followed by positioning balloon 38 over the guidewire.

Figure 2D:
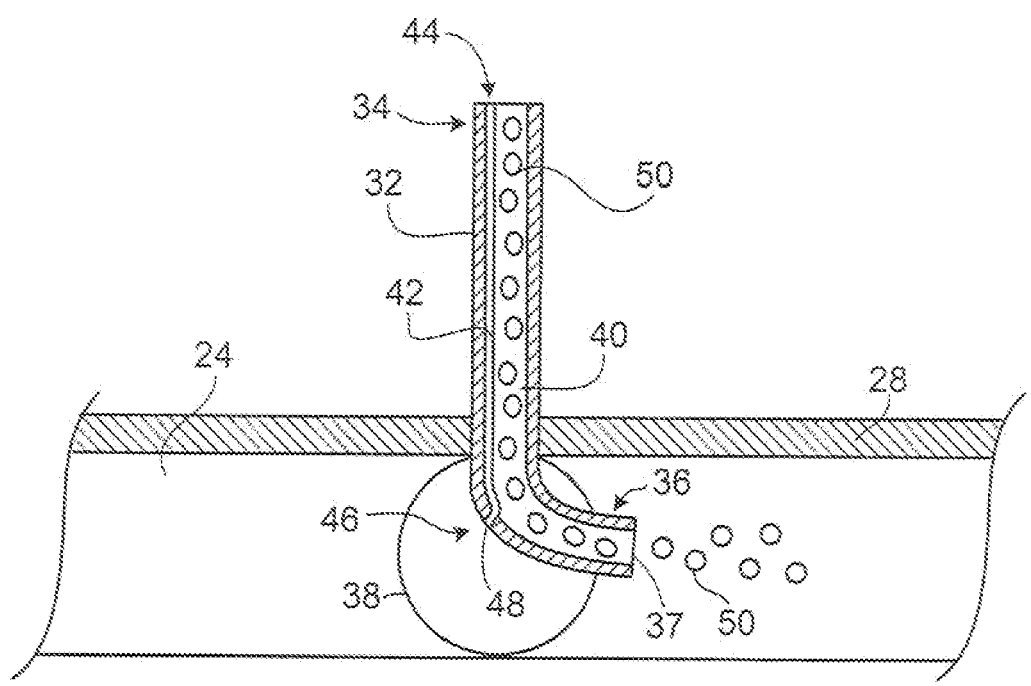
FIG. 2D illustrates the delivery of embolic material through the balloon catheter of FIG. 2C and into the lumen of the subject.

As shown in FIG. 2D, after balloon 38 has been inflated, embolic particles 50 are added into central lumen 40 of generally tubular member 32, and are delivered into branch 24 of portal vein 14. A sufficient volume of embolic particles 50 can be delivered into branch 24 to result in the embolization of branch 24. In some embodiments, embolic particles 50 can be disposed within a carrier fluid to form a composition (e.g., a suspension), which can be delivered through generally tubular member 32. The carrier fluid can be, for example, a pharmaceutically acceptable carrier, such as saline, contrast agent, therapeutic agent, or a combination of these carriers. In certain embodiments, the carrier fluid can include deionized water, water for injection, liquid polymer, gel polymer, gas, or a combination of these carriers. In certain embodiments, embolic particles 50 may not be suspended in a carrier fluid. For example, embolic particles 50 alone can be delivered through generally tubular member 32 and into branch 24.

Typically, the size of embolic particles 50 can be selected to provide sufficient embolization of a lumen of a subject, such as branch 24 of portal vein 14.

In some embodiments, one or more of embolic particles 50 can have a maximum dimension (e.g., a diameter) of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less; about 50 microns or less; about 10 microns or less; about five microns or less) and/or about one micron or more (e.g., about five microns or more; about microns or more; about 50 microns or more; about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more). For example, in certain embodiments, one or more of embolic particles 50 can have a maximum dimension (e.g., a diameter) of from about five microns to about 1,200 microns.

In certain embodiments, embolic particles 50 can have an arithmetic mean diameter of about 3,000 microns or less (e.g., about 2,500 microns or less; about 2,000 microns or less; about 1,500 microns or less; about 1,200 microns or less; about 1,000 microns or less; about 900 microns or less; about 700 microns or less; about 500 microns or less; about 400 microns or less; about 300 microns or less; about 100 microns or less; about 50 microns or less; about 10 microns or less; about five microns or less) and/or about one micron or more (e.g., about five microns or more; about 10 microns or more; about 50 microns or more; about 100 microns or more; about 300 microns or more; about 400 microns or more; about 500 microns or more; about 700 microns or more; about 900 microns or more; about 1,000 microns or more; about 1,200 microns or more; about 1,500 microns or more; about 2,000 microns or more; about 2,500 microns or more). The arithmetic mean diameter of a group of particles can be determined using a Beckman Coulter RapidVUE Image Analyzer version 2.06 (Beckman Coulter, Miami, Fla.). Briefly, the RapidVUE takes an image of continuous-tone (gray-scale) form and converts it to a digital form through the process of sampling and quantization. The arithmetic mean diameter of a group of particles (e.g., in a composition) can be determined by dividing the sum of the diameters of all of the particles in the group by the number of particles in the group.

Embolic particles 50 can be formed of any of a number of different materials. In some embodiments, embolic particles 50 can be formed of one or more polymers. Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides (e.g., alginate), polylactic acids, polyethylenes, polymethylmethacrylates, polycaprolactones, polyglycolic acids, poly(lactic-co-glycolic) acids (e.g., poly(d-lactic-co-glycolic) acids) and copolymers or mixtures thereof. In some embodiments, embolic particles 50 can be formed of one or more styrenic block copolymers, such as styrene-isobutylene-styrene block copolymer (SIBS).

Particles are described, for example, in Lanphere et al., U.S. Patent Application Publication No. US 2004/0096662 A1, published on May 20, 2004, and entitled "Embolization", DiCarlo et al., U.S. patent application Ser. No. 11/111,511, filed on Apr. 21, 2005, and entitled "Particles", Song et al., U.S. patent application Ser. No. 11/314,056, filed on Dec. 21, 2005, and entitled "Block Copolymer Particles", Song et al., U.S. patent application Ser. No. 11/314,557, filed on Dec. 21, 2005, and entitled "Block Copolymer Particles", and Song, U.S. patent application Ser. No. 11/355,301, filed on Feb. 15, 2006, and entitled "Block Copolymer Particles", all of which are incorporated herein by reference.

Figure 3A:
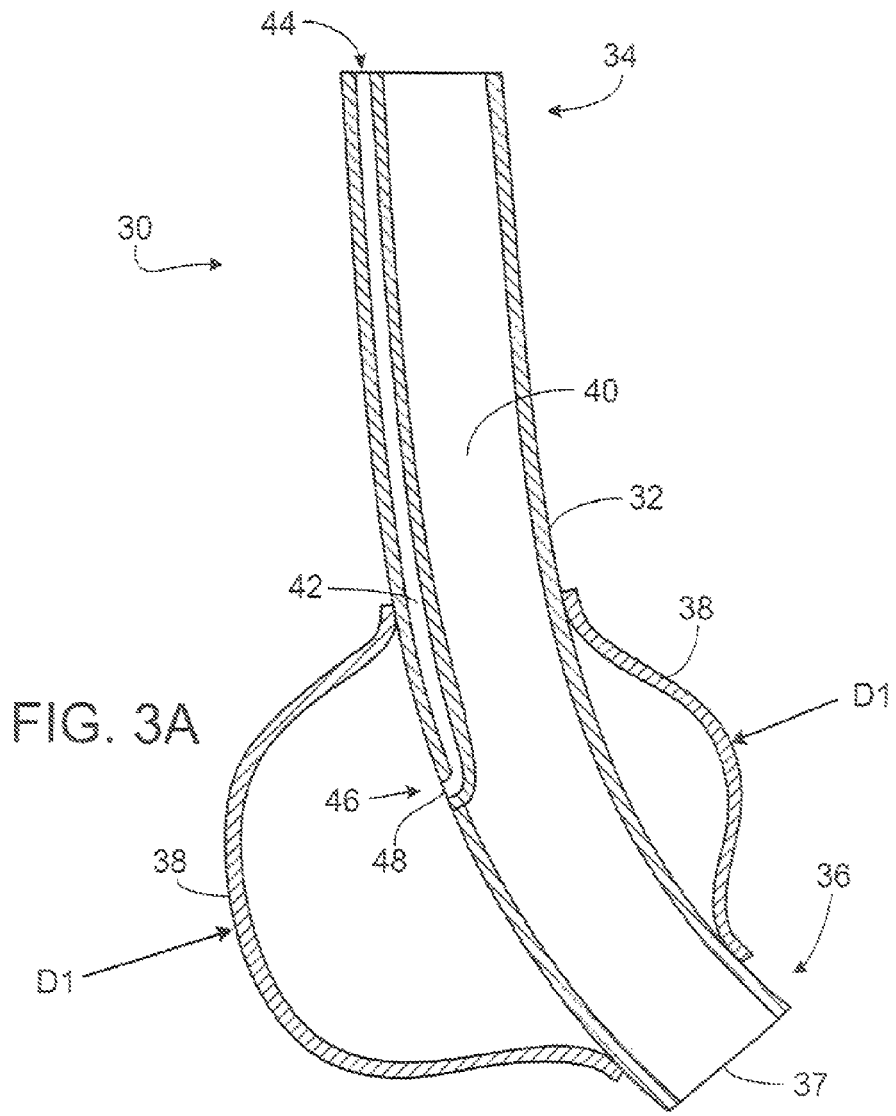
FIG. 3A is a cross-sectional view of an embodiment of a balloon catheter.

FIG. 3A shows an enlarged cross-sectional view of balloon catheter 30. As shown in FIG. 3A, balloon 38, which is eccentrically disposed on generally tubular member 32, has a diameter D1 when balloon 38 is inflated. In some embodiments, diameter D1 can be at least about five millimeters (e.g., at least about 10 millimeters, at least about 20 millimeters, at least about 30 millimeters) and/or at most about 40 millimeters (e.g., at most about 30 millimeters, at most about 20 millimeters, at most about 10 millimeters). In certain embodiments, diameter D1 can be from about 25 millimeters to about 33 millimeters.

Balloon 38 can be formed using, for example, a molding process. Typically, balloon 38 can be formed of one or more polymers (e.g., homopolymers, copolymers). Examples of polymers that can be used in balloon 38 include silicone, polyurethanes, polyesters (e.g., polyethylene terephthalate (PET) polymers, polybutylene terephthalate (PBT) polymers), polyamides (e.g., nylons such as aliphatic nylons and/or aromatic nylons), and polyethylenes. In some embodiments, balloon 38 can be formed of one or more polyether block polyamide copolymers. In certain embodiments, balloon 38 can be formed of latex. In some embodiments, balloon 38 can include a blend of polymers. Balloons (e.g., balloon materials) are described, for example, in Chin et al., U.S. Patent Application Publication No. US 2002/0165523 A1, published on Nov. 7, 2002, and entitled "Multilayer Medical Balloon", Pierre et al., U.S. Patent Application Publication No. US 2004/0078052 A1, published on Apr. 22, 2004, and entitled "Multilayer Medical Device", Chin et al., U.S. Pat. No. 6,951,675, and Sahatjian et al., U.S. Pat. No. 5,306,246, each of which is incorporated herein by reference.

Figure 3B:
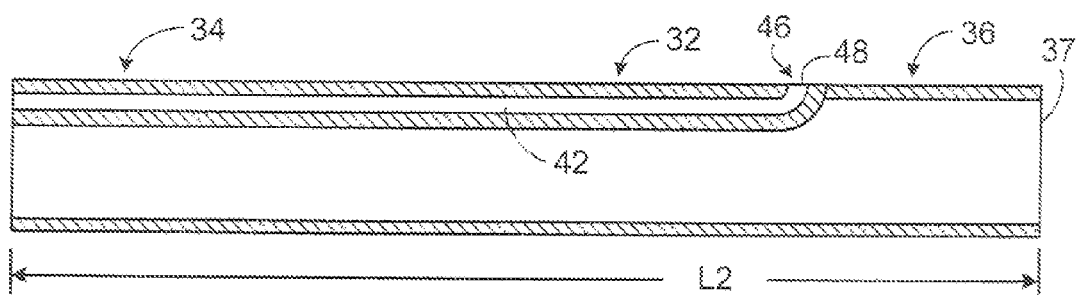
FIG. 3B is a cross-sectional view of a component of the balloon catheter of FIG. 3A.

FIG. 3B shows generally tubular member 32 in its straight form. As shown in FIG. 3B, when in its straight form, generally tubular member 32 has a length L2. In some embodiments (e.g., some embodiments in which generally tubular member 32 is designed to travel a relatively short distance within a body of a subject before reaching a target site), length L2 can be relatively short. In certain embodiments, length L2 can be at least about 10 centimeters (e.g., at least about 20 centimeters, at least about 30 centimeters) and/or at most about 40 centimeters (e.g., at most about 30 centimeters, at most about 20 centimeters). In some embodiments, length L2 can be about 30 centimeters.

Before generally tubular member 32 is inserted over needle 26, distal region 36 of generally tubular member 32 is curved.

The insertion of generally tubular member 32 over needle 26 causes distal region 36 to temporarily straighten. When needle 26 is subsequently removed from generally tubular member 32, distal region 36 re-assumes its curved form.

In certain embodiments, distal region 36 of generally tubular member 32 can be formed of one or more shape memory materials. Examples of shape memory materials include shape memory polymers, such as shape memory polyurethanes (available from Mitsubishi), polynorbornene (e.g., Norsorex™, available from Mitsubishi), polymethylmethacrylate (PMMA), poly(vinyl chloride), polyethylene (e.g., crystalline polyethylene), polyisoprene (e.g., trans-polyisoprene), styrene-butadiene copolymer, rubbers, or photocrosslinkable polymers including azo-dye, zwitterionic and/or other photochromic materials (as described in *Shape Memory Materials*, Otsuka and Wayman, Cambridge University Press, 1998). Additional examples of shape memory polymers include shape memory plastics available from MnemoScience GmbH Pauwelsstrasse 19, D-52074 Aachen, Germany.

In some embodiments, when a balloon such as balloon 38, which is eccentrically disposed on generally tubular member 32, is inflated, the eccentricity of the balloon can help to cause the distal region of the generally tubular member to become curved. As the larger side of the eccentrically disposed balloon expands, the expansion can cause the distal region of the generally tubular member to curve toward the smaller side of the eccentrically disposed balloon.

Figure 4:
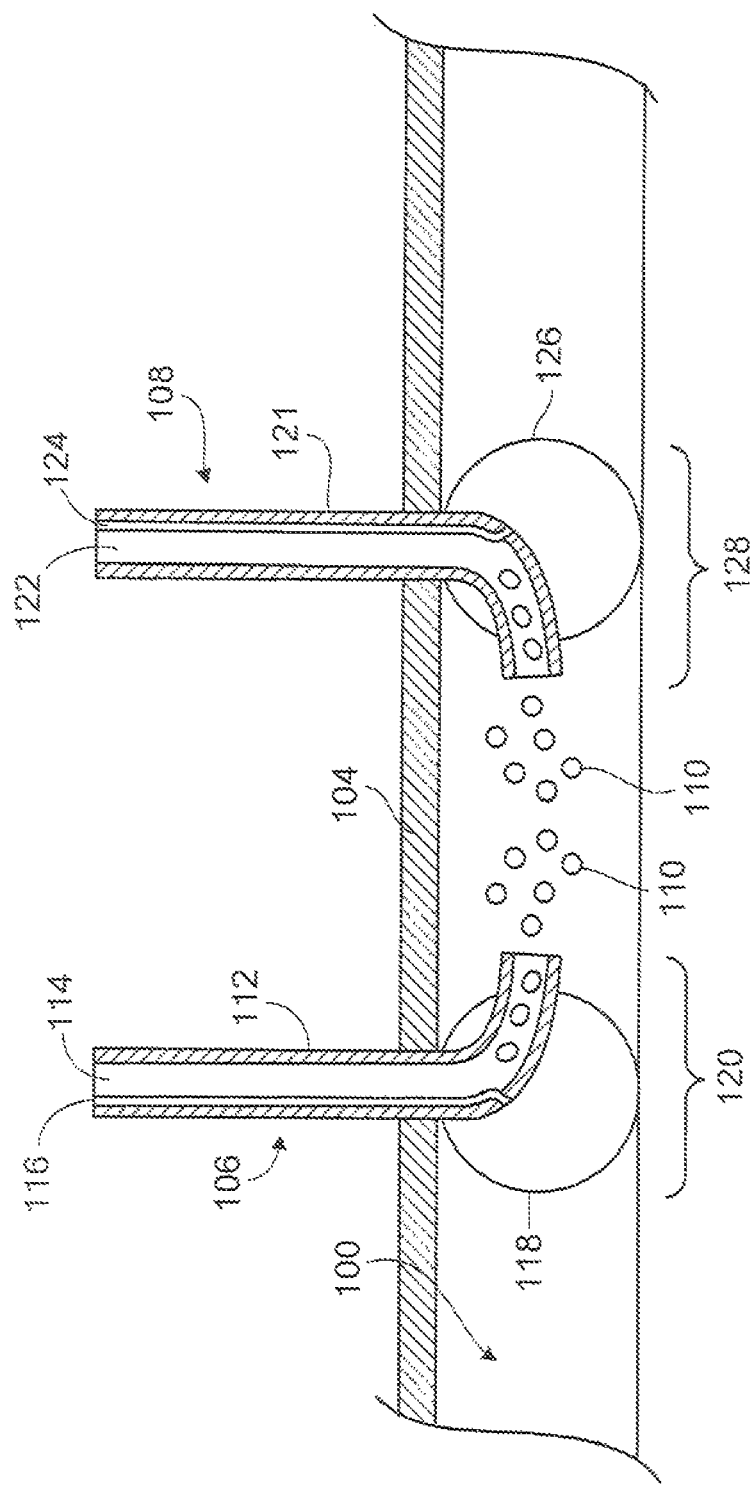
FIG. 4 illustrates the delivery of embolic material into a lumen of a subject.

In certain embodiments, multiple (e.g., two, three) balloon catheters can be used together in an embolization procedure. For example, FIG. 4 shows a branch 100 of a portal vein that is located beneath a layer 104 of skin and/or tissue. Two balloon catheters 106 and 108 have been inserted into branch 100, and are used to deliver embolic particles 110 into branch 100. As shown, balloon catheter 106 includes a generally tubular member 112 having a central lumen 114 and an inflation lumen 116, and also includes a balloon 118 that is in fluid communication with inflation lumen 116. Balloon 118 is inflated, and occludes a portion 120 of branch 100. Balloon catheter 108 includes a generally tubular member 121 having a central lumen 122 and an inflation lumen 124, and also includes a balloon 126 that is in fluid communication with inflation lumen 124. Balloon 126 is inflated, and occludes another portion 128 of branch 100. Embolic particles 110 are disposed into central lumens 114 and 122 of balloon catheters 106 and 108, and delivered into branch 100. The occlusion of portions 120 and 128 of branch 100 by balloons 118 and 126 provides a targeted region of branch 100 for embolization by embolic particles 110.

Figure 5A:
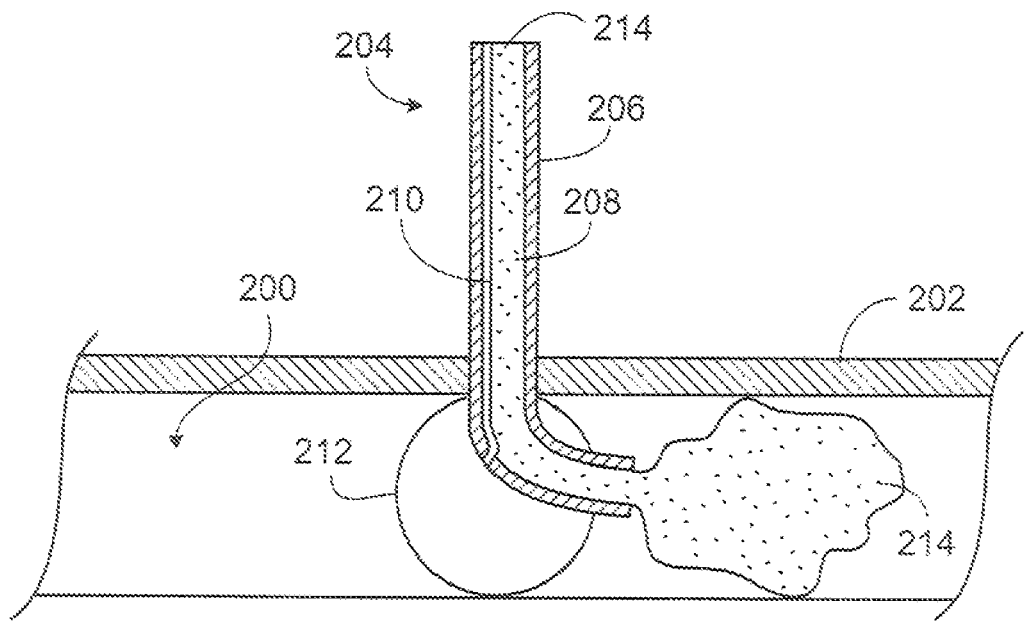
FIG. 5A illustrates the delivery of embolic material through an embodiment of a balloon catheter and into a lumen of a subject.
Figure 5B:
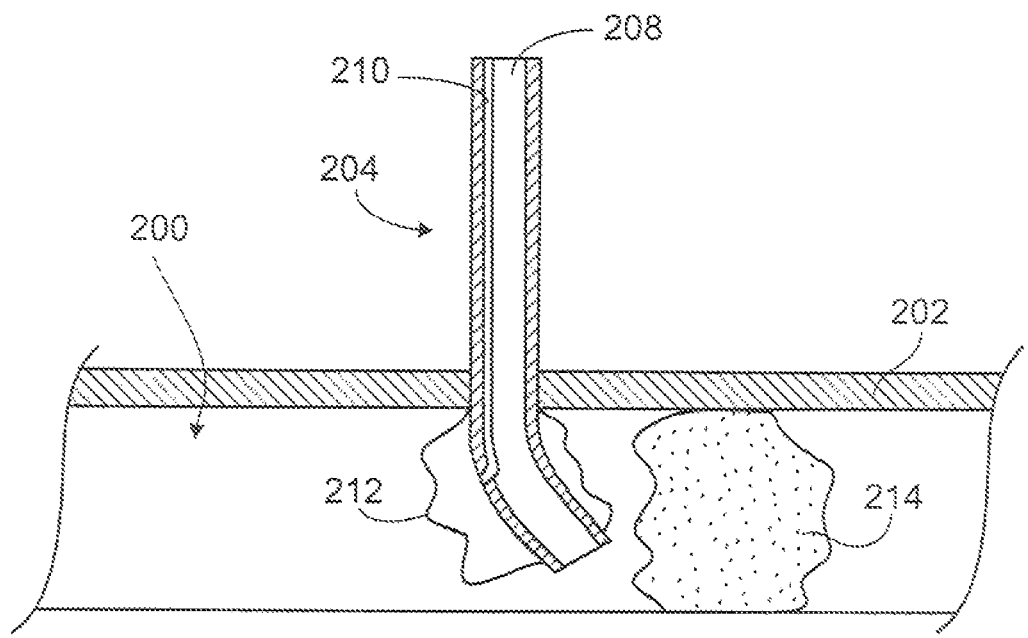
FIG. 5B illustrates the partial deflation of a balloon of the balloon catheter of FIG. 5A.
Figure 5C:
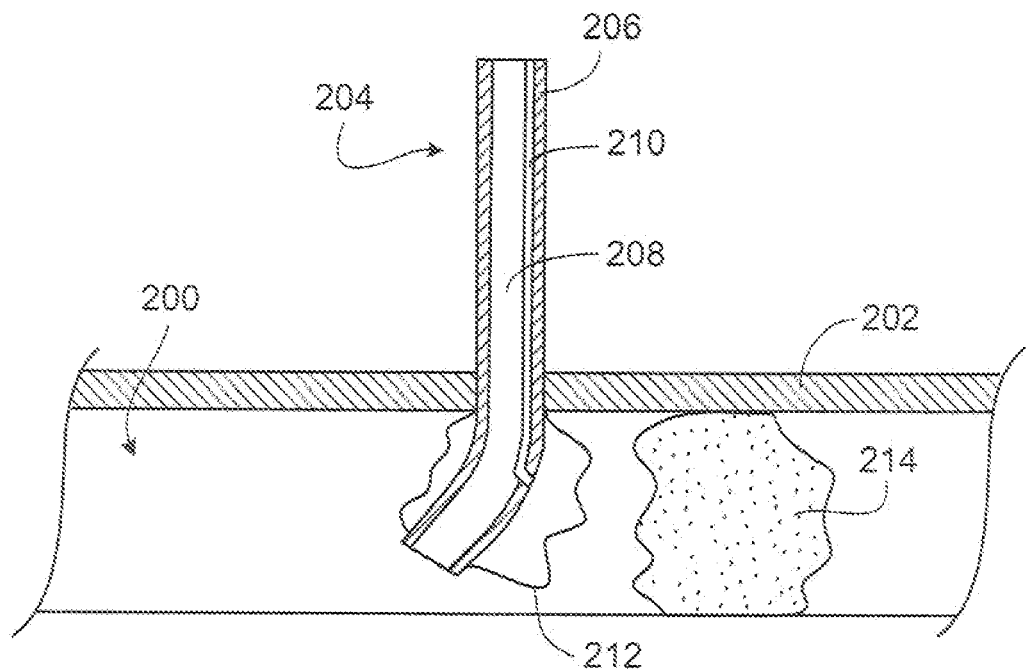
FIG. 5C illustrates the rotation of the partially deflated balloon of the balloon catheter of FIG. 5B within the lumen of the subject.
Figure 5D:
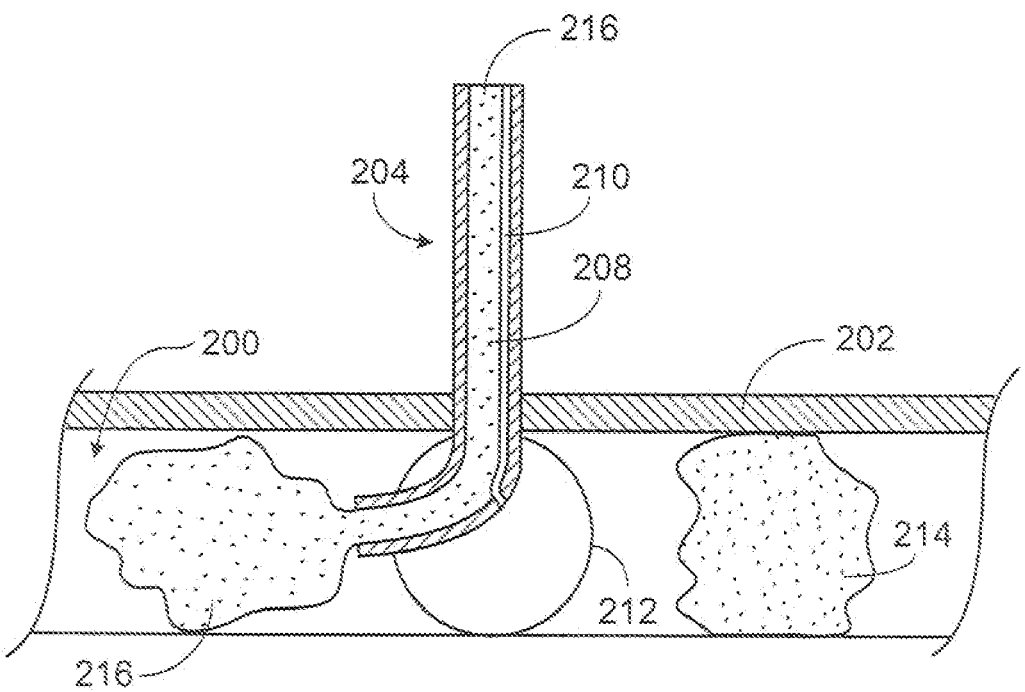
FIG. 5D illustrates the inflation of the balloon of the balloon catheter of FIG. 5C, and the delivery of embolic material through the balloon catheter and into the lumen of the subject.
Figure 5E:
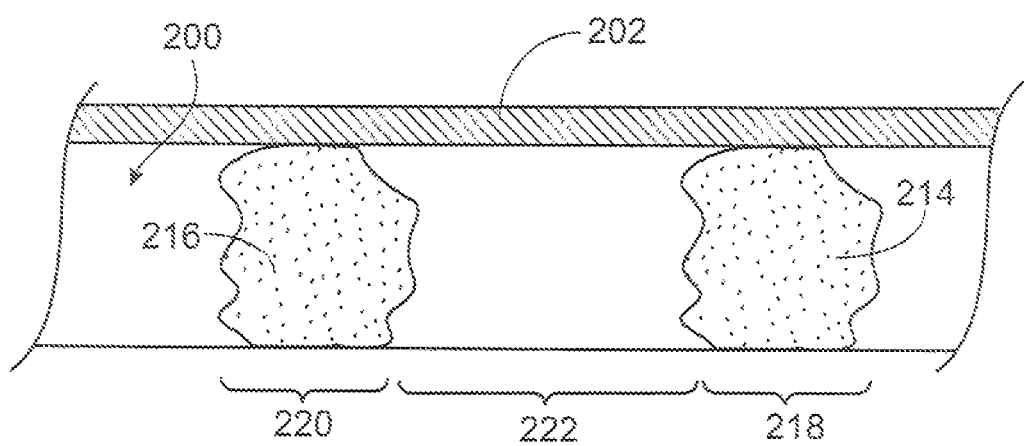
FIG. 5E is a cross-sectional view of the lumen of the subject of FIGS. 5A-5D, after embolic material has been delivered into the lumen of the subject.

In some embodiments, a balloon catheter can be used to define a target site for resection. For example, FIG. 5A shows a branch 200 of a portal vein in a body of a subject that is located beneath a layer 202 of skin and/or tissue. A balloon catheter 204 including a generally tubular member 206 having a central lumen 208 and an inflation lumen 210, and a balloon 212, has been inserted into branch 200. An embolic gel 214 is disposed into central lumen 208 of generally tubular member 206, and is delivered into branch 200. As shown in FIG. 5B, after embolic gel 214 has been delivered into branch 200, balloon 212 is slightly deflated, and, as shown in FIG. 5C, balloon catheter 204 is rotated 180 degrees. Thereafter, and as shown in FIG. 5D, an embolic gel 216 is disposed into central lumen 208 of generally tubular member 206, and is delivered into branch 200. Balloon catheter 204 is then removed from branch 200, which, as shown in FIG. 5E, includes a region 218 that is occluded by embolic gel 214, and a region 220 that is occluded by embolic gel 216. Embolic gels 214 and 216 can be formed of the same materials or of different materials. In certain embodiments, embolic gel 214 and/or embolic gel 216 can include one or more polymers. Embolic gels are described, for example, in U.S. Patent Application Publication No. US 2006/0045900 A1, published on Mar. 2, 2006, and entitled "Embolization", which is incorporated herein by reference.

In some embodiments, embolic gels 214 and 216 can include one or more radiopaque materials, materials that are visible by magnetic resonance imaging (MRI-visible materials), ferromagnetic materials, and/or contrast agents (e.g., ultrasound contrast agents). These materials can allow embolic gels 214 and 216 to be viewed using, for example, X-ray fluoroscopy, MRI, and/or ultrasound. When viewed using these techniques, embolic gels 214 and 216 can define a non-occluded region 222 between them. In certain embodiments, a physician can use non-occluded region 222 as a defined area in which resection can occur. Radiopaque materials, MRI-visible materials, ferromagnetic materials, and contrast agents are described, for example, in Rioux et al., U.S. Patent Application Publication No. US 2004/0101564 A1, published on May 27, 2004, and entitled "Embolization", which is incorporated herein by reference.

In some embodiments, a balloon catheter can be used in a procedure in which one or more therapeutic agents (e.g., a combination of therapeutic agents) are delivered into a target site in a body of a subject. In certain embodiments, the therapeutic agents can be incorporated into and/or onto embolic material that is delivered into the target site using the balloon catheter. In some embodiments, the therapeutic agents can provide a medium in which embolic material is delivered to a target site using the balloon catheter. In certain embodiments, the therapeutic agents and/or can be delivered to the target site independently of any embolic material.

Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; proteins; gene therapies; nucleic acids with and without carrier vectors (e.g., recombinant nucleic acids, DNA (e.g., naked DNA), cDNA, RNA, genomic DNA, cDNA or RNA in a non-infectious vector or in a viral vector which may have attached peptide targeting sequences, antisense nucleic acids (RNA, DNA)); oligonucleotides; gene/vector systems (e.g., anything that allows for the uptake and expression of nucleic acids); DNA chimeras (e.g., DNA chimeras which include gene sequences and encoding for ferry proteins such as membrane translocating sequences ("MTS") and herpes simplex virus-1 ("VP22")); compacting agents (e.g., DNA compacting agents); viruses; polymers; hyaluronic acid; proteins (e.g., enzymes such as ribozymes, asparaginase); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules, such as Y90 particles). Non-limiting examples of therapeutic agents include antithrombogenic agents; antioxidants; angiogenic and anti-angiogenic agents and factors; anti-proliferative agents (e.g., agents capable of blocking smooth muscle cell proliferation, such as rapamycin); calcium entry blockers (e.g., verapamil, diltiazem, nifedipine); and survival genes which protect against cell death (e.g., anti-apoptotic Bcl-2 family factors and Akt kinase).

Exemplary non-genetic therapeutic agents include: antithrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, acetyl salicylic acid, sulfasalazine and mesalamine; antineoplastic/antiproliferative/anti-mitotic agents such as paclitaxel, 5-fluorouracil, cisplatin, methotrexate, doxorubicin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet factors or peptides; vascular cell growth promoters such as growth factors, transcriptional activators, and translational promoters; vascular cell growth inhibitors such as growth factor inhibitors (e.g., PDGF inhibitor-Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor a, hepatocyte growth factor, and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or additionally, molecules capable of inducing an upstream or downstream effect of a BMP can be provided. Such molecules include any of the "hedgehog" proteins, or the DNA's encoding them. Vectors of interest for delivery of genetic therapeutic agents include: plasmids; viral vectors such as adenovirus (AV), adenoassociated virus (AAV) and lentivirus; and non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents are disclosed in Kunz et al., U.S. Pat. No. 5,733,925, which is incorporated herein by reference. Therapeutic agents disclosed in this patent include the following:

"Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

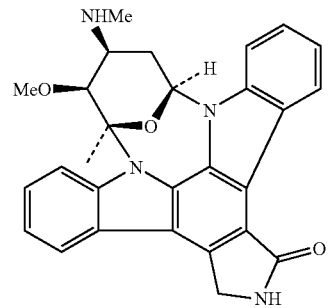 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

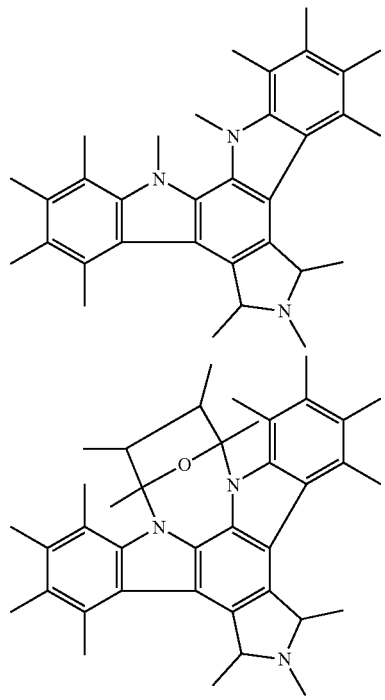

-continued

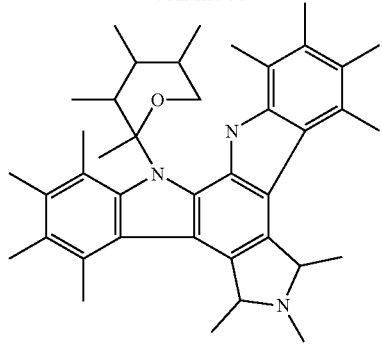

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like. Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell), such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, Pseudomonas exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, Pseudomonas exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents include one or more of the following: calcium-channel blockers, including benzothiazapines (e.g., diltiazem, clentiazem); dihydropyridines (e.g., nifedipine, amlodipine, nicardapine); phenylalkylamines (e.g., verapamil); serotonin pathway modulators, including 5-HT antagonists (e.g., ketanserin, naftidrofuryl) and 5-HT uptake inhibitors (e.g., fluoxetine); cyclic nucleotide pathway agents, including phosphodiesterase inhibitors (e.g., cilostazole, dipyridamole), adenylate/guanylate cyclase stimulants (e.g., forskolin), and adenosine analogs; catecholamine modulators, including α-antagonists (e.g., prazosin, bunazosine), β-antagonists (e.g., propranolol), and α/β-antagonists (e.g., labetalol, carvedilol); endothelin receptor antagonists; nitric oxide donors/releasing molecules, including organic nitrates/nitrites (e.g., nitroglycerin, isosorbide dinitrate, amyl nitrite), inorganic nitroso compounds (e.g., sodium nitroprusside), sydnonimines (e.g., molsidomine, linsidomine), nonoates (e.g., diazenium diolates, NO adducts of alkanediamines), S-nitroso compounds, including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), C-nitroso-, O-nitroso- and N-nitroso-compounds, and L-arginine; ACE inhibitors (e.g., cilazapril, fosinopril, enalapril); ATII-receptor antagonists (e.g., saralasin, losartin); platelet adhesion inhibitors (e.g., albumin, polyethylene oxide); platelet aggregation inhibitors, including aspirin and thienopyridine (ticlopidine, clopidogrel) and GP IIb/IIIa inhibitors (e.g., abciximab, epitifibatide, tirofiban, intergrilin); coagulation pathway modulators, including heparinoids (e.g., heparin, low molecular weight heparin, dextran sulfate, β-cyclodextrin tetradecasulfate), thrombin inhibitors (e.g., hirudin, hirulog, PPACK (D-phe-L-propyl-L-arg-chloromethylketone), argatroban), FXa inhibitors (e.g., antistatin, TAP (tick anticoagulant peptide)), vitamin K inhibitors (e.g., warfarin), and activated protein C; cyclooxygenase pathway inhibitors (e.g., aspirin, ibuprofen, flurbiprofen, indomethacin, sulfinpyrazone); natural and synthetic corticosteroids (e.g., dexamethasone, prednisolone, methprednisolone, hydrocortisone); lipoxygenase pathway inhibitors (e.g., nordihydroguairetic acid, caffeic acid; leukotriene receptor antagonists; antagonists of E- and P-selectins; inhibitors of VCAM-1 and ICAM-1 interactions; prostaglandins and analogs thereof, including prostaglandins such as PGE1 and PGI2; prostacyclins and prostacyclin analogs (e.g., ciprostene, epoprostenol, carbacyclin, iloprost, beraprost); macrophage activation preventers (e.g., bisphosphonates); HMG-CoA reductase inhibitors (e.g., lovastatin, pravastatin, fluvastatin, simvastatin, cerivastatin); fish oils and omega-3-fatty acids; free-radical scavengers/antioxidants (e.g., probucol, vitamins C and E, ebselen, retinoic acid (e.g., trans-retinoic acid), SOD mimics); agents affecting various growth factors including FGF pathway agents (e.g., bFGF antibodies, chimeric fusion proteins), PDGF receptor antagonists (e.g., trapidil), IGF pathway agents (e.g., somatostatin analogs such as angiopeptin and ocreotide), TGF-β pathway agents such as polyanionic agents (heparin, fucoidin), decorin, and TGF-β antibodies, EGF pathway agents (e.g., EGF antibodies, receptor antagonists, chimeric fusion proteins), TNF-α pathway agents (e.g., thalidomide and analogs thereof), thromboxane A2 (TXA2) pathway modulators (e.g., sulotroban, vapiprost, dazoxiben, ridogrel), protein tyrosine kinase inhibitors (e.g., tyrphostin, genistein, and quinoxaline derivatives); MMP pathway inhibitors (e.g., marimastat, ilomastat, metastat), and cell motility inhibitors (e.g., cytochalasin B); antiproliferative/antineoplastic agents including antimetabolites such as purine analogs (e.g., 6-mercaptopurine), pyrimidine analogs (e.g., cytarabine and 5-fluorouracil) and methotrexate, nitrogen mustards, alkyl sulfonates, ethylenimines, antibiotics (e.g., daunorubicin, doxorubicin, daunomycin, bleomycin, mitomycin, penicillins, cephalosporins, ciprofalxin, vancomycins, aminoglycosides, quinolones, polymyxins, erythromycins, tertacyclines, chloramphenicols, clindamycins, linomycins, sulfonamides, and their homologs, analogs, fragments, derivatives, and pharmaceutical salts), nitrosoureas (e.g., carmustine, lomustine) and cisplatin, agents affecting microtubule dynamics (e.g., vinblastine, vincristine, colchicine, paclitaxel, epothilone), caspase activators, proteasome inhibitors, angiogenesis inhibitors (e.g., endostatin, angiostatin and squalamine), and rapamycin, cerivastatin, flavopiridol and suramin; matrix deposition/organization pathway inhibitors (e.g., halofuginone or other quinazolinone derivatives, tranilast); endothelialization facilitators (e.g., VEGF and RGD peptide); and blood rheology modulators (e.g., pentoxifylline).

Other examples of therapeutic agents include anti-tumor agents, such as docetaxel, alkylating agents (e.g., mechlorethamine, chlorambucil, cyclophosphamide, melphalan, ifosfamide), plant alkaloids (e.g., etoposide), inorganic ions (e.g., cisplatin), biological response modifiers (e.g., interferon), and hormones (e.g., tamoxifen, flutamide), as well as their homologs, analogs, fragments, derivatives, and pharmaceutical salts.

Additional examples of therapeutic agents include organic-soluble therapeutic agents, such as mithramycin, cyclosporine, and plicamycin. Further examples of therapeutic agents include pharmaceutically active compounds, antisense genes, viral, liposomes and cationic polymers (e.g., selected based on the application), biologically active solutes (e.g., heparin), prostaglandins, prostcyclins, L-arginine, nitric oxide (NO) donors (e.g., lisidomine, molsidomine, NO-protein adducts, NO-polysaccharide adducts, polymeric or oligomeric NO adducts or chemical complexes), enoxaparin, Warafin sodium, dicumarol, interferons, interleukins, chymase inhibitors (e.g., Tranilast), ACE inhibitors (e.g., Enalapril), serotonin antagonists, 5-HT uptake inhibitors, and beta blockers, and other antitumor and/or chemotherapy drugs, such as BiCNU, busulfan, carboplatinum, cisplatinum, cytoxan, DTIC, fludarabine, mitoxantrone, velban, VP-16, herceptin, leustatin, navelbine, rituxan, and taxotere.

Therapeutic agents are described, for example, in DiMatteo et al., U.S. Patent Application Publication No. US 2004/0076582 A1, published on Apr. 22, 2004, and entitled "Agent Delivery Particle", and in Schwarz et al., U.S. Pat. No. 6,368,658, both of which are incorporated herein by reference.

While certain embodiments have been described, other embodiments are possible.

As an example, in some embodiments, a catheter can include a generally tubular member having a distal region that is not formed of a shape-memory material and/or that is not curved prior to being delivered into a lumen of a subject. In some embodiments, the distal region of the generally tubular member can be formed of one or more polymers having sufficient stiffness to allow the distal region to become curved. For example, in certain embodiments, the distal region can include one or more polymers (e.g., polyurethanes, polyethylenes, polyvinylchlorides, polyamide polyether block copolymers) having a hardness of, for example, from 55 Shore D durometer to 72 Shore D durometer. The distal region can become curved (e.g., after the generally tubular member has been inserted into a lumen of a subject) by inserting a device into the lumen of the generally tubular member, and manipulating the device within the lumen such that the device causes the distal region to become curved.

As another example, in certain embodiments, a catheter can include a balloon having a relatively thick portion and a relatively thin portion. For example, the catheter can include a balloon having one portion with a thickness of at most about 0.006 inch, and another portion with a thickness of at least about 0.001 inch. When the balloon is inflated, the relatively thick portion of the balloon can experience less overall inflation than the relatively thin portion of the balloon. The greater extent of inflation of the relatively thin portion of the balloon can cause the distal region of the generally tubular member to assume a curved shape. In some embodiments, a balloon having portions with different thicknesses can be formed using a two-step molding process. First, a balloon mold (in the form of a mandrel) is oriented vertically and dipped into a solution of a balloon material, to form a relatively even layer of balloon material over the mold. The layer of balloon material is then allowed to dry, and thereafter the mold is rotated into a horizontal position, and is only partially dipped into the balloon material solution to form a second layer on a portion of the balloon. Once the balloon material has dried, the balloon can be removed from the mold.

As an additional example, in certain embodiments, a catheter can include a balloon having different portions that are formed of different materials. The result can be that the different portions of the balloon inflate at different rates when inflation fluid is added into the balloon. This differential inflation can cause the distal region of a generally tubular member of the catheter to become curved.

As another example, while particles and gels have been described as examples of embolic materials, in some embodiments, one or more other devices and/or materials can be used to embolize a target site. For example, in some embodiments, a mixture of N-butyl-2-cyanoacrylate (NBCA) ethiodized oil, and/or a mixture of fibrin glue with ethiodized oil, can be used to embolize a lumen of a subject, such as a branch of a portal vein. In certain embodiments, one or more coils can be used in an embolization procedure. In some embodiments, a target site can be embolized using particles, and at the end of the embolization procedure, a relatively small number of coils can be added into the target site. In certain embodiments, the coils can have enhanced visibility under ultrasound relative to the particles, and can be used to determine the location of the embolized region under ultrasound. Coils are described, for example, in Elliott et al., U.S. patent application Ser. No. 11/000,741, filed on Dec. 1, 2004, and entitled "Embolic Coils", and in Buiser et al., U.S. patent application Ser. No.

11/311,617, filed on Dec. 19, 2005, and entitled "Coils", both of which are incorporated herein by reference.

As a further example, while the delivery of embolic material using a balloon catheter has been described, in some embodiments, one or more other types of materials can alternatively or additionally be delivered into a body of a subject using a balloon catheter. For example, in certain embodiments, one or more contrast agents, such as one or more radiopaque and/or MRI contrast agents, can be delivered into a body of a subject using a balloon catheter. Examples of radiopaque contrast agents include Omnipaque™, Renocal®, iodiamide meglumine, diatrizoate meglumine, ipodate calcium, ipodate sodium, iodamide sodium, iothalamate sodium, iopamidol, and metrizamide. Radiopaque contrast agents are commercially available from, for example, Bracco Diagnostic. Examples of MRI contrast agents include superparamagnetic iron oxides (e.g., ferumoxides, ferucarbotran, ferumoxsil, ferumoxtran (e.g., ferumoxtran-10), PEG-feron, ferucarbotran); gadopentetate dimeglumine; gadoterate meglumine; gadodiamide; gadoteridol; gadoversetamide; gadobutrol; gadobenate dimeglumine; mangafodipir trisodium; gadoxetic acid; gadobenate dimeglumine; macromolecular Gd-DOTA derivate; gadobenate dimeglumine; gadopentetate dimeglumine; ferric ammonium citrate; manganese chloride; manganese-loaded zeolite; ferristene; perfluoro-octylbromide; and barium sulfate. MRI contrast agents are described, for example, in Zhong et al., U.S. Patent Application Publication No. US 2004/0186377 A1, published on Sep. 23, 2004, and entitled "Medical Devices", which is incorporated herein by reference. In some embodiments, one or more therapeutic agents, such as one or more of the therapeutic agents described above, can be delivered into the body of a subject using a balloon catheter.

As another example, while the use of a balloon catheter and embolic material in a portal vein embolization procedure has been described, in some embodiments, a balloon catheter and/or embolic material can be used in one or more other procedures. For example, a balloon catheter and/or embolic material can be used in a procedure to treat one or more sites having cancerous lesions, such as the breast, prostate, lung, thyroid, or ovaries. A balloon catheter and/or embolic material can be used in, for example, neural, pulmonary, and/or AAA (abdominal aortic aneurysm) applications. A balloon catheter and/or embolic material can be used in the treatment of, for example, fibroids, tumors, internal bleeding, arteriovenous malformations (AVMs), and/or hypervascular tumors. A balloon catheter and/or embolic material can be used in, for example, a procedure that is used to fill one or more aneurysm sacs, AAA sac (Type II endoleaks), endoleak sealants, arterial sealants, and/or puncture sealants, and/or can be used to provide occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels (e.g. in the brain) which shunt blood from a high pressure artery to a low pressure vein, resulting in hypoxia and malnutrition of those regions from which the blood is diverted. In certain embodiments, a balloon catheter and/or embolic material can be used to prophylactically treat a condition.

In some embodiments, a catheter including a balloon can be used in a mitral valve repair procedure. For example, in certain embodiments, the balloon can be inflated and used to section off a portion of the mitral valve that is to be treated. In some embodiments, a catheter including a balloon can be used to tighten a mitral valve. In certain embodiments, a balloon that is used in a mitral valve procedure can have a diameter of at least about 0.5 inch and/or at most about 0.8 inch. In general, the mitrial valve can be entered from below or from above. The distal end of the catheter can be manipulated to a target site where, for example, a suturing/stapling device can be passed through, and secure the tissue to tighten the valve.

In certain embodiments, the arithmetic mean diameter of particles that are delivered to a subject through a balloon catheter can vary depending upon the particular condition to be treated. As an example, in certain embodiments in which the particles are used to embolize a liver tumor, the particles delivered to the subject can have an arithmetic mean diameter of about 500 microns or less (e.g., from about 100 microns to about 300 microns; from about 300 microns to about 500 microns). As another example, in some embodiments in which the particles are used to embolize a uterine fibroid, the particles delivered to the subject can have an arithmetic mean diameter of about 1,200 microns or less (e.g., from about 500 microns to about 700 microns; from about 700 microns to about 900 microns; from about 900 microns to about 1,200 microns). As an additional example, in certain embodiments in which the particles are used to treat a neural condition (e.g., a brain tumor) and/or head trauma (e.g., bleeding in the head), the particles delivered to the subject can have an arithmetic mean diameter of less than about 100 microns (e.g., less than about 50 microns). As a further example, in some embodiments in which the particles are used to treat a lung condition, the particles delivered to the subject can have an arithmetic mean diameter of less than about 100 microns (e.g., less than about 50 microns). As another example, in certain embodiments in which the particles are used to treat thyroid cancer, the particles can have a diameter of about 1,200 microns or less (e.g., from about 1,000 microns to about 1,200 microns).

As a further example, in some embodiments, particles having different shapes, sizes, physical properties, and/or chemical properties, can be used together in an embolization procedure. The different particles can be delivered into the body of a subject in a predetermined sequence or simultaneously. In some embodiments, particles having different shapes and/or sizes can be capable of interacting synergistically (e.g., by engaging or interlocking) to form a well-packed occlusion, thereby enhancing embolization. Particles with different shapes, sizes, physical properties, and/or chemical properties, and methods of embolization using such particles are described, for example, in Bell et al., U.S. Patent Application Publication No. US 2004/0091543 A1, published on May 13, 2004, and entitled "Embolic Compositions", and in DiCarlo et al., U.S. Patent Application Publication No. US 2005/0095428 A1, published on May 5, 2005, and entitled "Embolic Compositions", both of which are incorporated herein by reference.

As an additional example, while balloons having generally spherical inflated shapes have been shown, in some embodiments, a balloon can have a non-spherical inflated shape. For example, in certain embodiments, a balloon can have a cylindrical or ellipsoidal inflated shape. The shape of a balloon can be selected, for example, based on the shape of the region the balloon is designed to treat.

As a further example, in certain embodiments, a catheter can include a balloon having multiple (e.g., two, three, four, five) layers. Balloons with multiple layers are described, for example, in Chin et al., U.S. Patent Application Publication No. US 2002/0165523 A1, published on Nov. 7, 2002, and entitled "Multilayer Medical Balloon", Pierre et al., U.S. Patent Application Publication No. US 2004/0078052 A1, published on Apr. 22, 2004, and entitled "Multilayer Medical Device", and Chin et al., U.S. Patent Application Publication No. US 2004/0146670 A1, published on Jul. 29, 2004, and entitled "Multilayer Balloon Catheter", each of which is incorporated herein by reference.

As an additional example, while the use of a needle to temporarily straighten the distal region of a generally tubular member of a balloon catheter has been described, in some embodiments, one or more other devices can alternatively or additionally be used to temporarily straighten the distal region of a generally tubular member. For example, in certain embodiments, a guidewire and/or a stylet can be used to temporarily straighten the distal region of a generally tubular member.

As a further example, in some embodiments, a balloon catheter can be delivered into a target site (e.g., a lumen of a subject, such as a portal vein) through an introducer sheath.

As another example, in certain embodiments, a balloon catheter can be delivered into a target site, and a microcatheter can then be delivered into a lumen of a generally tubular member of the balloon catheter. Thereafter, embolic material (e.g., embolic particles) can be delivered into the target site through the microcatheter.

As a further example, while a catheter including a generally tubular member having two lumens has been described, in some embodiments, a catheter can include a generally tubular member having more than two lumens (e.g., three lumens, four lumens).

As another example, in some embodiments, a catheter can include a generally tubular member having coaxial lumens. For example, a catheter can include a generally tubular member having a central lumen and an inflation lumen that are coaxial.

As a further example, in certain embodiments, a lumen of a subject can have a longitudinal axis, and a needle and/or a balloon catheter can be inserted into the lumen at an angle that is not perpendicular to the longitudinal axis.

As an additional example, while embolic gels including one or more radiopaque materials, MRI-visible materials, ferromagnetic materials, and/or contrast agents have been described, in some embodiments, embolic particles and/or coils can include one or more of these materials.

Other embodiments are in the claims.

What is claimed is:

1. A method for embolizing one or more branches of a portal vein for slowing or stopping blood flow to segments of a liver, the method comprising:
   delivering a catheter into a branch of the portal vein of a subject, the catheter comprising:
      a generally tubular member having a proximal region and a distal region, the generally tubular member defining a lumen, and
      an inflatable member carried by a portion of the generally tubular member;
   inflating the inflatable member to occlude the branch of the portal vein and to curve the portion of the generally tubular member that carries the inflatable member within the branch of the portal vein of the subject such that the portion of the generally tubular member that carries the inflatable member extends in a first direction generally along the branch of the portal vein of the subject;
   disposing at least one first embolic material into the lumen of the generally tubular member and delivering the at least one first embolic material into the branch of the portal vein of the subject to slow or stop blood flow to a first segment of the liver and to redirect the blood flow to a second segment of the liver,
   after delivering the at least one first embolic material, deflating the inflatable member,
   after deflating the inflatable member, rotating the portion of the generally tubular member that carries the inflatable member within the branch of the portal vein of the subject,
   after rotation, inflating the inflatable member to curve the portion of the generally tubular member that carries the inflatable member within the branch of the portal vein of the subject such that the portion of the generally tubular member that carries the inflatable member extends in a second direction generally along the branch of the portal vein of the subject, the second direction generally opposite the first direction, and then
   disposing at least one second embolic material into the lumen of the generally tubular member and delivering the at least one second embolic material into the branch of the portal vein of the subject to slow or stop blood flow to the first segment of the liver and to redirect the blood flow to the second segment of the liver.

2. The method of claim 1, wherein the at least one first embolic material is selected from the group consisting of embolic gels, embolic particles, embolic coils, and combinations thereof.

3. The method of claim 1, wherein the at least one first embolic material comprises embolic particles.

4. The method of claim 3, wherein the embolic particles have an arithmetic mean diameter of about 3,000 microns or less.

5. The method of claim 4, wherein the embolic particles have the arithmetic mean diameter of about one micron or more.

6. The method of claim 1, wherein the at least one first embolic material comprises an embolic gel.

7. The method of claim 1, wherein the inflatable member has a wall comprising a first region having a first thickness and a second region having a second thickness that is different from the first thickness.

8. The method of claim 1, wherein the inflatable member is eccentrically disposed on the portion of the generally tubular member that carries the inflatable member.

9. The method of claim 1, wherein the inflatable member has a diameter of at least about five millimeters when inflated.

10. The method of claim 9, wherein the inflatable member has the diameter of at most about 40 millimeters when inflated.

11. The method of claim 1, wherein the method further comprises resecting a liver tissue of the subject.

12. The method of claim 1, wherein the branch of the portal vein of the subject defines a longitudinal axis, and delivering the catheter into the branch of the portal vein of the subject comprises inserting the catheter into the branch of the portal vein of the subject along an axis that is perpendicular to the longitudinal axis.

13. The method of claim 12, wherein the at least one first embolic material comprises embolic particles.

14. The method of claim 1, wherein delivering the catheter into the branch of the portal vein of the subject comprises inserting the catheter through a first location in skin of the subject and inserting the catheter through a second location in the branch of the portal vein of the subject, and the second location is located at most about three millimeters from the first location.

15. The method of claim 1, wherein curving the portion of the generally tubular member that carries the inflatable member comprises aligning the portion of the generally tubular member that carries the inflatable member with a longitudinal axis of the branch of the portal vein of the subject in the first direction; and
  wherein rotating the portion of the generally tubular member that carries the inflatable member comprises aligning the portion of the generally tubular member that carries the inflatable member with the longitudinal axis of the branch of the portal vein of the subject in the second direction generally opposite the first direction.

16. A method for embolizing one or more branches of a portal vein for slowing or stopping blood flow to segments of a liver, the method comprising:
  inserting a needle through a layer of skin and/or a tissue and into a branch of the portal vein of a subject such that the needle is generally perpendicular to a longitudinal axis of the branch of the portal vein;
  delivering a catheter over the needle into the branch of the portal vein of the subject through the layer of skin and/or the tissue, the catheter comprising:
    a generally tubular member having a proximal region and a distal region, the generally tubular member defining a lumen, and
    an inflatable member carried by a portion of the generally tubular member;
  inflating the inflatable member to occlude the branch of the portal vein and to curve the portion of the generally tubular member that carries the inflatable member within the branch of the portal vein of the subject such that the portion of the generally tubular member that carries the inflatable member extends in a first direction generally along the branch of the portal vein of the subject;
  disposing at least one first embolic material into the lumen of the generally tubular member and delivering the at least one first embolic material into the branch of the portal vein of the subject to slow or stop the blood flow to the segments of the liver,
  after delivering the at least one first embolic material, deflating the inflatable member,
  after deflating the inflatable member, rotating the portion of the generally tubular member that carries the inflatable member within the branch of the portal vein of the subject,
  after rotation, inflating the inflatable member to curve the portion of the generally tubular member that carries the inflatable member within the branch of the portal vein of the subject such that the portion of the generally tubular member that carries the inflatable member extends in a second direction generally along the branch of the portal vein of the subject, the second direction generally opposite the first direction, and then
  disposing at least one second embolic material into the lumen of the generally tubular member and delivering the at least one second embolic material into the branch of the portal vein of the subject.

17. The method of claim 16, wherein the at least one first embolic material is selected from the group consisting of embolic gels, embolic particles, embolic coils, and combinations thereof.

18. The method of claim 16, wherein the at least one first embolic material comprises embolic particles.

19. The method of claim 18, wherein the embolic particles have an arithmetic mean diameter of about 3,000 microns or less.

20. The method of claim 19, wherein the embolic particles have the arithmetic mean diameter of about one micron or more.

21. The method of claim 16, wherein the at least one first embolic material comprises an embolic gel.

22. The method of claim 16, wherein the inflatable member has a wall comprising a first region having a first thickness and a second region having a second thickness that is different from the first thickness.

23. The method of claim 16, wherein the inflatable member is eccentrically disposed on the portion of the generally tubular member that carries the inflatable member.

24. A method for treating a liver of a patient, the method comprising:
  providing a catheter having a distal portion, the catheter having a balloon disposed at the distal portion;
  advancing the catheter through a portal vein of the liver;
  inflating the balloon;
  wherein inflating the balloon curves the distal portion of the catheter and occludes the portal vein;
  infusing an embolic material through the catheter into one or more branches of the portal vein to slow or stop blood flow to a first portion of the liver;
  wherein infusing the embolic material through the catheter into the one or more branches of the portal vein to slow or stop the blood flow to the first portion of the liver includes redirecting the blood flow to a second portion of the liver; and
  resecting the first portion of the liver.

25. The method of claim 24, wherein redirecting the blood flow to the second portion of the liver initiates hypertrophy of the second portion of the liver.

26. The method of claim 24, wherein redirecting the blood flow to the second portion of the liver initiates exaggerated growth of the second portion of the liver.

* * * * *